United States Patent [19]

Gaffar et al.

[11] Patent Number: 4,931,273
[45] Date of Patent: * Jun. 5, 1990

[54] ANTICALCULUS ORAL COMPOSITION

[75] Inventors: Abdul Gaffar, Princeton; Thomas G. Polefka, Somerset; Robert J. Ferlauto, Jr., Edison; Rosemarie M. Crisafulli, East Windsor, all of N.J.

[73] Assignee: Colgate-Palmolive Company, Piscataway, N.J.

[*] Notice: The portion of the term of this patent subsequent to Dec. 9, 2003 has been disclaimed.

[21] Appl. No.: 437,715

[22] Filed: Nov. 16, 1989

Related U.S. Application Data

[63] Continuation of Ser. No. 312,532, Feb. 17, 1989, Pat. No. 4,906,456, which is a continuation of Ser. No. 842,101, Mar. 20, 1986, Pat. No. 4,806,877, which is a continuation-in-part of Ser. No. 775,851, Sep. 13, 1985, Pat. No. 4,627,977.

[51] Int. Cl.$^5$ ............................ A61K 7/16; A61K 7/18
[52] U.S. Cl. ............................................ 424/52; 424/57
[58] Field of Search ................................. 424/52-57

[56] References Cited

U.S. PATENT DOCUMENTS

| 3,429,963 | 2/1969 | Shedlovsky | 424/56 |
|---|---|---|---|
| 4,323,551 | 4/1982 | Parran | 424/57 |
| 4,340,583 | 7/1982 | Wason | 424/52 |
| 4,421,527 | 12/1983 | Wason | 424/52 |
| 4,515,772 | 5/1985 | Parran et al. | 424/57 |
| 4,590,066 | 5/1986 | Parran et al. | 424/52 |
| 4,627,977 | 12/1986 | Gaffar et al. | 424/52 |
| 4,661,341 | 4/1987 | Benedict et al. | 424/49 |
| 4,806,340 | 2/1989 | Gaffar et al. | 424/52 |
| 4,806,342 | 2/1989 | Gaffar et al. | 424/52 |
| 4,808,400 | 2/1989 | Gaffar et al. | 424/52 |
| 4,808,401 | 2/1989 | Gaffar et al. | 424/52 |
| 4,822,599 | 4/1989 | Mitra et al. | 424/52 |
| 4,842,847 | 6/1989 | Amjad | 424/52 |
| 4,847,070 | 7/1989 | Pyrz et al. | 424/52 |
| 4,869,898 | 9/1989 | Gaffar et al. | 424/52 |
| 4,880,619 | 11/1989 | Gaffar et al. | 424/52 |
| 4,885,155 | 12/1989 | Parran et al. | 424/52 |
| 4,889,712 | 12/1989 | Gaffar et al. | 424/52 |
| 4,889,713 | 12/1989 | Gaffar et al. | 424/52 |
| 4,892,724 | 1/1990 | Amjad | 424/52 |
| 4,892,725 | 1/1990 | Amjad | 424/52 |
| 4,894,220 | 1/1990 | Nabi et al. | 424/52 |
| 4,906,456 | 3/1990 | Gaffar et al. | 424/52 |

FOREIGN PATENT DOCUMENTS

| 1233121 | 2/1988 | Canada . |
| 0254452 | 1/1988 | European Pat. Off. . |
| 295116 | 12/1988 | European Pat. Off. . |
| 0297211 | 1/1989 | European Pat. Off. . |
| 0297212 | 1/1989 | European Pat. Off. . |
| 0297213 | 1/1989 | European Pat. Off. . |
| 0311412 | 4/1989 | European Pat. Off. . |
| 0319516 | 6/1989 | European Pat. Off. . |
| 2188548 | 10/1987 | United Kingdom . |
| 2201593 | 9/1988 | United Kingdom . |
| 2204487 | 11/1988 | United Kingdom . |

Primary Examiner—Shep K. Rose
Attorney, Agent, or Firm—Murray M. Grill; Robert L. Stone; Robert C. Sullivan

[57] ABSTRACT

An oral dentifrice composition such as a toothpaste, dental gel, toothpowder, dental tablet or lozenge containing as anticalculus agent about 4.3% to about 7% of alkali metal pyrophosphates comprising at least 4.3% of tetrapotassium pyrophosphate alone or admixed with up to 2.7% of tetrasodium pyrophoshpate, and as inhibitors against enzymatic hydrolysis of such agent in saliva, a fluoride and preferably up to about 3% of a synthetic anionic polymeric polycarboxylate, and use of such composition in a program of oral hygiene and/or for inhibiting dental calculus.

20 Claims, No Drawings

ANTICALCULUS ORAL COMPOSITION

This is a continuation, of application Ser. No. 07/312,532 filed 2/17/89 now U.S. Pat. No. 4,906,456 which is a continuation of application Ser. No. 06/842,101 filed 3/20/86, now U.S. Pat. No. 4,806,877, which was a continuation-in-part of application Ser. No. 06/775,851 filed 9/13/85, now U.S. Pat. No. 4,627,977. The entire disclosure of said application Ser. No. 775,851 is incorporated herein by reference.

This invention relates to oral compositions containing an anticalculus agent.

Calculus is a hard, mineralized formation which forms on the teeth. Regular brushing aids in preventing a rapid build-up of these deposits, but even regular brushing is not sufficient to remove all of the calculus deposits which adhere to the teeth. Calculus is formed on the teeth when crystals of calcium phosphates begin to be deposited in the pellicle and extracellular matrix of the dental plaque and become sufficiently closely packed together for the aggregates to become resistant to deformation. There is no complete agreement on the route by which calcium and orthophosphate ultimately become the crystalline material called hydroxyapatite (HAP). It is generally agreed, however, that at higher saturations, that is, above the critical saturation limit, the precursor to crystalline HAP is an amorphous or microcrystalline calcium phosphate. "Amorphous calcium phosphate" although related to hydroxyapatite differs from it in atomic structure, particle morphology, and stoichiometry. The X-ray diffractoin pattern of amorphous calcium phosphate shows broad peaks typical of amorphous materials, which lack the long-range atomic order characteristic of all crystalline materials, including HAP. It is apparent therefore that agents which effectively interfere with crystalline growth of HAP will be effective as anticalculus agents. A suggested mechanism by which the anticalculus agents of this invention inhibit calculus formation probably involves an increase of the activation energy barrier thus inhibiting the transformation of precursor amorphous calcium phosphate to HAP.

Studies have shown that there is a good correlation between the ability of a compound to prevent HAP crystalline growth in vitro and its ability to prevent calcification in vivo, provided of course that such compound is stable in plaque, saliva and their components.

The prior art indicates that soluble pyrophosphate may be utilized to reduce calculus formation. For example, U.S. Pat. No. 4,515,772 issued May 7, 1985 to Parran et al refers to several prior art references disclosing oral compositions containing soluble pyrophosphate salts, including an article by Draus et al, Arch. Oral. Biol., 15, pp 893-896, (1970), which discloses the in vitro effectiveness of such salts against calculus. The article refers to possible inhibition of pyrophosphate by pyrophosphatase enzyme.

It is known that saliva contains acid phosphatase, alkaline phosphatase and pyrophosphatase enzymes. It is considered that any one of the three enzymes may adversely affect pyrophosphates as an inhibitor of HAP formation and calculus. It is accordingly apparent that an anticalculus pyrophosphate dentifrice composition, should inhibit, reduce or nullify the destructive activity of all three salivary enzymes.

The compositions of the aforementioned Parran et al patent are limited to a pH of 6.0 to 10.0 and comprise a fluoride and soluble dialkali metal pyrophosphates alone or admixed with tetraalkali metal pyrophosphates, but no more than 4.0% $K_4P_2O_7$ (tetrapotassium pyrophosphate).

Said parent application Ser. No. 775,851 is concerned with oral compositions containing as anticalculus agent one or a mixture of linear molecularly dehydrated polyphosphate salts, including dialkali metal and tetraalkali metal pyrophosphates and as combination inhibitor against enzymatic hydrolysis of said agent in saliva, a fluoride ion source and a synthetic anionic linear polymeric polycarboxylate. As stated therein, compounds providing a source of fluoride ion have been profusely disclosed in the prior art as anti-caries agent but not for inhibiting salivary hydrolysis of linear polyphosphate salts employed as anticalculus agents. For example, in an article by G. W. Rapp et al in J. Dent. Res. 39, 372-376 (1960) entitled "Pyrophosphate: A Factor in Tooth Erosion", the erosive effects of relatively large amounts of pyrophosphate accumulating in saliva and salivary debris in contact with tooth substance in producing eroded lesions on enamel, exposed dentin and cementum was studied. In these studies, fluoride from NaF was employed to inhibit hydrolysis of pyrophosphate by pyrophosphatase enzyme and thus permit accumulation of the pyrophosphate to determine its tooth erosion effects.

It is an object of this invention to provide an improved dentifrice composition containing one or a mixture of pyrophosphate salts as essential anticalculus (antitartar) agent.

Another object of this invention is to provide such a composition containing one or more inhibitors against enzymatic hydrolysis of said agent in saliva.

Still another object of this invention is to provide such a composition effective over a relatively wide pH range and/or with improved cosmetic properties.

A further object of this invention is to provide such a composition which does not significantly erode tooth surfaces and which also exerts substantial and acceptable anti-caries effects.

Yet a further object of this invention is the provision of an improved method for inhibiting the formation of calculus. Other objects and advantages will appear as the description proceeds.

Earlier in the development of this invention, it was found that dentifrice compositions containing only tetrasodium pyrophosphate as anticalculus agent were gritty, and that the solid gritty particles were composed of undissolved $Na_4P_2O_7$.

The present invention is at least in part based on our determinations or discoveries that fluoride ion inhibits hydrolysis of pyrophosphate by acid phosphatase and pyrophosphatase enzymes, that the synthetic anionic polymeric polycarboxylate salts referred to in said parent application Ser. No. 775,851 inhibit hydrolysis of pyrophosphate by alkaline phosphatase, and that the occurrence of gritty particles in the oral compositions can be avoided by employing a predominant portion of the pyrophosphate in the form of the tetrapotassium salt.

In accordance with certain of its aspects, this invention relates to a dentifrice composition in the form of a toothpaste, dental gel, toothpowder, dental tablet or lozenge containing an orally acceptable vehicle and, in approximate weight proportions, A. 4.3% to 7% of alkali metal pyrophosphates as essential anticalculus agent, comprising at least 4.3% of tetrapotassium pyrophosphate, alone or admixed with up to 2.7% of tetrasodium pyrophosphate, and as inhibitors against enzymatic hydrolysis of said agent in saliva,
B. an amount of a fluoride ion source sufficient to supply 25 ppm. to 5,000 ppm. of fluoride ions, and
C. 0% to 3% of a synthetic anionic polymeric polycarboxylate having a molecular weight of about 1,000 to about 1,000,000.

Synthetic anionic polymeric polycarboxylates and their complexes with various cationic germicides, zinc and magnesium have been previously disclosed as anticalculus agents per se in, for example U.S. Pat. No. 3,429,963 to Shedlovsky and instant assignee, U.S. Pat. No. 4,152,420 to Gaffar and instant assignee, U.S. Pat. No. 3,956,480 to Dichter et al and instant assignee, U.S. Pat. No. 4,138,477 to Gaffar and instant assignee, and U.S. Pat. No. 4,183,914 to Gaffar et al. None of these patents however nor any other known prior art, discloses use of such polycarboxylates alone for inhibiting salivary hydrolysis of pyrophosphate anticalculus agents, much less in combination with a compound providing a source of fluoride ion. It is to be understood that the synthetic anionic polymeric polycarboxylates per se disclosed in these patents are operative in the compositions and methods of this invention and such disclosures are to that extent incorporated herein by reference thereto.

The synthetic anionic polymeric polycarboxylates optionally but preferably employed herein are, as indicated above, well known, being employed in the form of their free acids or partially or preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. These copolymers are available for example as Gantrez (AN 139 (M.W. 500,000), A.N. 119 (M.W. 250,000) and preferably S-97 Pharmaceutical Grade (M.W. 70,000), of GAF Corporation. The term "synthetic" is intended to exclude known thickening or gelling agents comprising carboxymethyl-cellulose and other derivatives of cellulose and natural gums. Also excluded are the zinc, magnesium and similar metal complexes of these polymeric polycarboxylates.

Other operative polymeric polycarboxylates include those disclosed in U.S. Pat. No. 3,956,480 referred to above, such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000, and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates disclosed in above referred to U.S. Pat. Nos. 4,138,477 and 4,183,914, include copolymers of maleic anhydride with styrene, isobutylene or ethyl vinyl ether, polyacrylic, polyitaconic and polymaleic acids, and sulfoacrylic oligomers of M.W. as low as 1,000, available as Uniroyal ND-2.

Suitable generally are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, furmaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

Also useful herein are carboxyvinyl polymers, disclosed as toothpaste components in U.S. Pat. No. 3,980,767 issued September 14, 1976 to Choun et al, U.S. Pat. No. 3,935,306 issued January 27, 1976 to Roberts et al, U.S. Pat. No. 3,919,409 issued November 11, 1975 to Perla et al, U.S. Pat. No. 3,911,904 issued October 7, 1975 to Harrison, and U.S. Pat. No. 3,711,604 issued January 16, 1973 to Colodney et al. They are commercialcially available for example under the trademarks Carbopol 934,940 and 941 of B. F. Goodrich, these products consisting essentially of a colloidally water-soluble polymer of polyacrylic acid crosslinked with from about 0.75% to about 2.0% of polyallyl sucrose or polyallyl pentaerythritol as cross-linking agent.

The synthetic anionic polymeric polycarboxylate component is mainly a hydrocarbon with optional halogen and O-containing substituents and linkages as present in for example ester, ether and OH groups, and when present is generally employed in the instant compositions in approximate weight amounts of 0.05 to 3%, preferably 0.05 to 2%, more preferably 0.1 to 2%. Amounts in the upper portions of these ranges are typically employed in dentifrice compositions typically containing a dental abrasive and used in conjunction with brushing of the teeth, e.g. tooth pastes (including creams), gels, powders and tablets. Amounts in excess of these ranges may be employed for thickening or gelling purposes.

As indicated above, these polymeric polycarboxylates have been found to be effective inhibitors of alkaline phosphatase enzyme. Since this enzyme has little activity (for hydrolyzing pyrophosphate) at about pH 7.0 or below, the polymeric polycarboxylate component may, if desired, be omitted from oral preparations formulated to operate at such pH of 7.0 or below. Such omission however obviously reduces the versatility and effectiveness of the present oral compositions over the broad pH range of about 4.5 to about 10.

The sources of fluoride ions, or fluoride providing compounds, required according to this invention as an essential acid phosphatase and pyrophophatase enzyme inhibitor component are well known in the art as anticaries agents and also act as such agents in the practice of this invention. These compounds may be slightly soluble in water or may be fully water-soluble. They are characterized by their ability to release fluoride ions in water and by freedom from undesired reaction with other compounds of the oral preparation. Among these materials are inorganic fluoride salts, such as soluble alkali metal, alkaline earth metal salts, for example, sodium fluoride, potassium fluoride, ammonium fluoride, calcium fluoride, a copper fluoride such as cuprous fluoride, zinc fluoride, barium fluoride, sodium fluorsilicate, ammonium fluorosilicate, sodium fluorozirconate, sodium monofluorophosphate, aluminum mono- and di-fluorophosphate, and fluorinated sodium calcium pyrophosphate. Alkali metal and tin fluorides, such as sodium and stannous fluorides, sodium monofluorophosphate (MFP) and mixtures thereof, are preferred.

The amount of fluoride providing compound is dependent to some extent upon the type of compound, its solubility, and the type of oral preparation, but it must be a nontoxic amount, generally about 0.005 to about 3.0% in the preparation. In a dentifrice preparation, e.g. dental gel, toothpaste (including cream), toothpowder, or dental tablet, an amount of such compound which releases up to about 5,000 ppm of F ion by weight of the preparation is considered satisfactory. Any suitable minimum amount of such compound may be used, but it is preferable to employ sufficient compound to release about 300 to 2,000 ppm, more preferably about 800 to about 1,500 ppm of fluoride ion. Typically, in the cases of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount of about 0.1–3%, more typically about 0.76%.

In dentifrice preparations such as lozenges and chewing gum, the fluoride providing compound is typically present in an amount sufficient to release up to about 500 ppm, preferably about 25 to 300 ppm by weight of fluoride ion. Generally about 0.005 to about 1.0 wt. % of such compound is present.

The dentifrice compositions of this invention achieve the desired anticalculus effect by mixing therein about 4.3% to about 7% of tetrapotassium pyrophosphate alone or with up to 2.7% of tetrasodium pyrophosphate. Preferred ratios of the tetrapotassium:tetrasodium salts range from about 4.3:2.7 to about 6:1, especially a ratio of 4.5:1.5. Contrary to the disclosure in the aforementioned Parran et al patent, it is highly significant that the compositions of this invention have highly acceptable anticalculus and improved cosmetic properties while including more than 4.0% of the tetrapotassium pyrophosphate and without inclusion of any dialkali metal pyrophosphate, although small amounts thereof, such as about 0.1% to about 0.4% or about 1.0% may be so included if desired.

The pH of the dentifrice preparations of this invention is generally in the range of from about 4.5 to about 10 and typically from about 5.5 to 9. The pH is preferably in the range of from about 6 to about 8.0. It is noteworthy that the compositions of the invention may be applied orally at said pH ranges without substantially decalcifying or otherwise damaging dental enamel. The pH can be controlled with acid (e.g. citric acid or benzoic acid) or base (e.g. sodium hydroxide) or buffered (as with sodium citrate, benzoate, carbonate, or bicarbonate, disodium hydrogen phosphate, sodium dihydrogen phosphate, etc.).

In certain desirable forms of this invention, the dentifrice composition may be substantially solid or pasty in character, such as toothpowder, a dental tablet, a toothpaste (cream), or a dental gel. The vehicle of such solid or pasty dentifrice preparations typically contains an orally or dentally acceptable polishing material for use in conjunction with a brushing of the teeth. Examples of such polishing materials are water-insoluble sodium metaphosphate, potassium metaphosphate, tricalcium phosphate, dihydrate calcium phosphate, anhydrous dicalcium phosphate, calcium pyrophosphate, magnesium orthophosphate, trimagnesium phosphate, calcium carbonate, aluminum silicate, zirconium silicate, silica, bentonite, and mixtures thereof. Other suitable polishing materials include the particulate thermosetting resins described in U.S. Pat. No. 4,070,510 of December 15, 1962 such as melamine-, phenolic-, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 cm.$^2$/gm., silica gel or colloidal silica, and complex amorphous alkali metal alumino-silicate.

When visually clear gels are desired, a polishing agent of colloidal silica, such as those sold under the trademark SYLOID as Syloid 72 and Syloid 74 or under the trademark SANTOCEL as Santocel 100 and alkali metal aluminosilicate complexes are particularly useful, since they have refractive indices close to the refractive indices of gelling agent-liquid (including water and/or humectant) systems commonly used in dentifrices.

Many of the so-called "water-insoluble" polishing materials are anionic in character and also include small amounts of soluble material. Thus, insoluble sodium metaphosphate may be formed in any suitable manner as illustrated by Thorpe's *Dictionary of Applied Chemistry*, Volume 9, 4th Edition, pp. 510–511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than about 1% of the material is larger than about 37 microns.

The polishing material is generally present in the solid or pasty compositions in weight concentrations of about 10% to about 99%. Preferably, it is present in amounts ranging from about 10% to about 75% in toothpaste or gel and from about 70% to about 99% in toothpowder or tablet.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol (e.g. 400–600) exemplify suitable humectants/carriers. Also advantageous are liquid mixtures of water, glycerine and sorbitol. In clear gels where the refractive index is an important consideration, about 3–30 wt. % of water, 0 to about 80 wt. % of glycerine, and about 20–80 wt. % of sorbitol is preferably employed.

Toothpastes (creams) and gels typically contain a natural or synthetic thickener or gelling agent in proportions of about 0.1 to about 10, preferably about 0.5 to about 5, wt. %. A suitable thickener is synthetic hectorite, a synthetic colloidal magnesium alkali metal silicate complex clay available for example as Laponite (e.g.

CP, SP 2002, D) marketed by Laporte Industries Limited. Laponite D analysis shows, approximately by weight, 58.00% $SiO_2$, 25.40% $MgO$, 3.05% $Na_2O$, 0.98% $Li_2O$, and some water and trace metals. Its true specific gravity is 2.53 and it has an apparent bulk density (g./ml. at 8% moisture) of 1.0.

Other suitable thickeners include Irish moss, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244).

It will be understood that, as is conventional, the oral preparations are to be sold or otherwise distributed in suitable labelled packages. Thus, a toothpaste, cream or gel will usually be in a collapsible tube, typically aluminum, lined lead or plastic, or other squeeze, pump or pressurized dispenser for metering out the contents, having a label describing it, in substance, as a toothpaste, gel or dental cream.

Organic surface-active agents are used in the compositions of the present invention to achieve increased prophylactic action, assist in achieving thorough and complete dispersion of the anticalculus agent throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

Various other materials may be incorporated in the oral preparations of this invention such as whitening agents, preservatives, silicones, chlorophyll compounds, other anticalculus agents, and/or ammoniated material such as urea, diammonium phosphate, and mixtures thereof. These adjuvants, where present, are incorporated in the preparations in amounts which do not substantially adversely affect the properties and characteristics desired. Significant amounts of zinc, magnesium and other metal salts and materials, generally soluble, which would complex with the active components of the instant invention are to be avoided.

Any suitable flavoring or sweetening material may also be employed. Examples of suitable flavoring constituents are flavoring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, dextrose, levulose, sorbitol, xylitol, d-tryptophan, dihydrochalcones, sodium cyclamate, perillartine, APM (aspartyl phenyl alanine, methyl ester), saccharine and the like. Suitably, flavor and sweetening agents may together comprise from about 0.1% to 5% or more of the preparation.

In the preferred practice of this invention an oral composition according to this invention such as dentifrice containing the described pyrophosphate and enzyme inhibitor in an amount effective to inhibit calculus on dental surfaces is preferably applied as by brushing regularly to dental enamel, such as every second or third day or preferably from 1 to 3 times daily, at a pH of about 4.5 to about 10, generally about 5.5 to about 9, preferably about 6 to 8, for at least 2 weeks up to 8 weeks or more up to lifetime. The dentifrice is typically removed by rinsing with water after each application.

The compositions of this invention can be incorporated in lozenges, or in chewing gum or other products, e.g. by stirring into a warm gum base or coating the outer surface of a gum base, illustrative of which may be mentioned jelutone, rubber latex, vinylite resins, etc., desirably with conventional plasticizers or softeners, sugar or other sweeteners or carbohydrates such as glucose, sorbitol and the like.

The vehicle or carrier in a tablet or lozenge is a non-cariogenic solid water soluble polyhydric alcohol (polyol) such as mannitol, xylitol, sorbitol, maltitol, a hydrogenated starch hydrolysate, Lycasin, hydrogenated glucose, hydrogenated disaccharides, and hydrogenated polysaccharides, in an amount of about 90–98% by weight of the total composition. Solid salts such as sodium bicarbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and carbowax.

Lozenge formulations contain about 2% gum as barrier agent to provide a shiny surface as opposed to a tablet which has a smooth finish. Suitable non-cariogenic gums include Kappa carrageenan, carboxymethyl cellulose, hydroxyethyl cellulose, Gantrez, and the like.

The lozenge or tablet may optionally be coated with a coating material such as waxes, shellac, carboxymethyl cellulose, polyethylene/maleic anhydride copolymer or Kappacarrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact of the teeth in the oral cavity with the active ingredients.

The following examples are further illustrative of the nature of the present invention, but it is understood that the invention is not limited thereto. All amounts and proportions referred to herein and in the appended claims are by weight and temperatures are in degrees C. unless otherwise indicated.

EXAMPLE A

Effect of Salivary Enzymes on Inhibition of HAP Formation by TSPP

The in vitro formation of HAP is measured titrimetrically via a pH stat procedure. Stock solutions of 0.1M $CaCl_2$ and 0.1M $NaH_2PO_4$ are prepared fresh in carbonate-free deionized distilled water. To 23 ml $CO_2$-free deionized distilled water 1.0 ml. of the stock phosphate solution and 1.0 ml. of an aqueous solution of $1 \times 10^{-4}$ of the anticalculus agent being tested are added followed by 1.0 ml. of the stock calcium chloride solution which initiates the reaction. The reaction is conducted at pH 7.4 under a nitrogen atmosphere. Consumption of 0.1N NaOH is recorded automatically from which the time required for crystal formation is determined. Table A shows the results of this procedure.

TABLE A

| Anticalculus Agent | Time of Crystal Growth Inhibition (Hrs.) | | | |
|---|---|---|---|---|
| | Water | Saliva | Pyro-Phosphatase | Alk. Phosphatase |
| TSPP* | 0.8 | 0.4 | 0.3 | 0.0 |

*Tetrasodium pyrophosphate

Table A shows that in water TSPP significantly delays HAP formation. However, the effectiveness of this agent is drastically reduced when incubated with saliva as evidenced by the shorter delay time. This reduction in efficacy is due to the enzymatic hydrolysis of P—O—P bonds. Incubation of this agent with pyrophosphatase and alkaline phosphatase drastically reduces the delay period and indicates the susceptibility of the P—O—P bond to hydrolysis by phosphatases. Substantially the same results are obtained using tetrapotassium pyrophosphate (TKPP) instead of TSPP, both having the same effective P—O—P bond-containing pyrophosphate ion.

EXAMPLE B

Stabilization of TSPP to Enzymatic Hydrolysis in Presence of Inhibitors

Enzymatic hydrolysis is conducted in 100 millimolar morpholinopropane sulfonic acid—NaOH buffer solution (pH 7.0) containing 1.3 mg./ml of TSPP. Inhibitors of this invention are added (except to the control) to a final concentration of 1,000 ppm fluoride ion (from NaF) and 0.5% of the sodium salt of hydrolyzed methoxyethylene-maleic anhydride (1:1) copolymer, M.W. 70,000 (Gantrez S-97 Pharmaceutical Grade). Equal activities of acid phosphatase, alkaline phosphatase, and inorganic pyrophosphatase are then added to yield a total phosphatase activity of 0.3 units/ml. Samples of the test solution are taken and total orthophosphate available in each sample measured after 3 hours hydrolysis in 4N HCl at 100° C. The reaction mixture is incubated at 37° C. with shaking and aliquots taken at appropriate times through at least 90 minutes for orthophosphate determination. Table 1 shows the results expressed as percent orthophosphate released due to hydrolysis of the pyrophosphate.

TABLE B

| Anticalculus Agent | Percent Orthophosphate Released in 90 min. | | Percent Relative Protection |
|---|---|---|---|
| | Control | With Inhibitors | |
| TSPP | 98 | 58 | 41 |

Table B shows that after 90 min. incubation in the presence of enzyme 98% of the available orthophosphate is released from the TSPP in the absence of the inhibitors. With inhibitors, hydrolysis of P—O—P bonds in pyrophosphate (TSPP) is reduced by 41%. It should be noted that the enzyme activities used in this study are at least 2-3 fold greater than those normally found in saliva. These data indicate that the inhibitors of this invention significantly reduce enzymatic hydrolysis of TSPP. Substantially the same results are obtained when equivalent amounts of TKPP is substituted for the TSPP.

The following dental gel formulations are representative of the invention. Example 1 is a white opacified gel, Example 2 is a blue transparent gel.

| | Parts by Weight | |
|---|---|---|
| | Example 1 | Example 2 |
| Part 1 | | |
| TSPP | 1.500 | 1.500 |
| TKPP | 4.500 | 4.500 |
| Sorbitol (70% Aqueous Solution) | 22.507 | 22.500 |
| Part 2 | | |
| Polyethylene Glycol 600 | 5.000 | 5.000 |
| Glycerine | 10.750 | 15.000 |
| IOTA Carrageenan Gum | 0.500 | 0.450 |
| Sodium Fluoride | 0.243 | 0.243 |
| Sodium Saccharin | 0.300 | 0.300 |
| Gantrez S-97 | 1.000 | 1.000 |
| Titanium Dioxide | 0.500 | — |
| Deionized Water | 31.000 | 26.607 |
| FD&C Blue #1 (1% Solution) | — | 0.200 |
| Part 3 | | |
| ZEO 49B ($SiO_2$) | 17.000 | 16.000 |
| SYLOID 244 (Synthetic Silica) | 3.000 | 4.500 |
| Part 4 | | |
| Sodium Lauryl Sulfate Powder | 1.200 | 1.200 |
| Flavor | 1.000 | 1.000 |

The above formulations are prepared as follows: The components of Part 1 are mixed to solution form. Separately, the components of Part 2, except the water, are mixed to form a dispersion in the polyethylene glycol/glycerin humectant, and the water then mixed in. Parts 1 and 2 are then combined, followed by consecutive addition, with suitable mixing, of Parts 3 and 4. These and the following formulations are designed to retain the anti-caries effect of the fluoride component substantially unaffected by the other components, and to produce no significant tooth erosion effects.

EXAMPLE 3

Employing the same procedure as in Examples 1 and 2, the following toothpaste formulation is prepared in accordance with this invention.

| Ingredient | Parts by Weight |
| --- | --- |
| Deionized water | 37.578 |
| Glycerin | 25.000 |
| Zeo 49B (Silicon Dioxide) | 21.500 |
| TKPP | 4.500 |
| TSPP | 1.500 |
| Syloid 244 (synthetic silica) | 3.000 |
| Sodium Lauryl Sulfate | 1.200 |
| Flavor | 1.000 |
| Gantrez S-97 Pharmaceutical Grade | 1.000 |
| Sodium Hydroxide (50% Solution) | 1.000 |
| Xanthan Gum | 1.000 |
| Sodium Benzoate | 0.500 |
| Titanium Dioxide | 0.500 |
| Sodium Saccharin | 0.300 |
| Sodium Fluoride | 0.242 |

Examples 4 and 5 represent lozenge formulations according to the invention.

Example 4
Lozenge Formulations

| | Parts by Weight |
| --- | --- |
| Sugar | 75–98 |
| Cornsyrup | 1–20 |
| Flavor Oil | 0.1–1.0 |
| Tablet lubricant | 0.1–5 |
| TKPP:TSPP-3:1 | 3.5–8 |
| Gantrez S-97 | 0.05–3 |
| NaF | 0.01–0.05 |
| Water | 0.01–0.2 |

Example 5
Lozenge

| | Weight Percent |
| --- | --- |
| Sodium saccharin | 0.15 |
| Flavor | 0.25 |
| Magnesium stearate lubricant | 0.40 |
| Color | 0.01 |
| Emulsifying Agent* | 1.00 |
| NaF | 0.05 |
| Gantrez S-97 | 0.30 |
| TKPP:TSPP-3:1 | 6.50 |
| Sorbitol | QS to 100 |

*PEG (40) Sorbitan Diisostearate

Example 6
Chewing Gum

| | Parts |
| --- | --- |
| Gum base | 10 to 50 |
| Binder | 3 to 10 |
| Filler (sorbitol, mannitol or combination thereof) | 5 to 80 |
| Artificial sweetener | 0.1 to 5 |
| TKPP:TSPP-3:1 | 3.5 to 8 |
| Gantrez S-97 | 0.1 to 1.0 |
| NaF | 0.1 to 0.05 |
| Flavor | 0.1 to 5 |

All the above formulations have been designed to provide improved non-gritty and other cosmetic properties and to exert improved anticalculus effects in vivo.

This invention has been described with respect to certain preferred embodiments and it will be understood that modifications and variations thereof obvious to those skilled in the art are to be included within the purview of this application and the scope of the appended claims.

We claim:

1. In an oral composition containing an orally acceptable aqueous vehicle and, in approximate weight amounts and proportions,
   A. a mixture of tetrasodium pyrophosphate and tetrapotassium pyrophosphate;
   B. an amount of a fluoride ion source sufficient to supply 25 ppm to 5,000 ppm of fluoride ions; and
   C. about 0.05 to about 3% of a synthetic anionic polymeric polycarboxylate having a molecular weight of about 1,000 to about 1,000,000,
the improvement in which the tetrapotassium pyrophosphate is a predominant portion of said mixture.

2. In an oral composition containing an orally acceptable aqueous vehicle and, in approximate weight amounts and proportions,
   A. a mixture of alkali metal pyrophosphates containing tetrasodium pyrophosphate and tetrapotassium pyrophosphate;
   B. an amount of a fluoride ion source sufficient to supply 25 ppm to 5,000 ppm of fluoride ions; and
   C. about 0.05 to about 3% of a synthetic anionic polymeric polycarboxylate having a molecular weight of about 1,000 to about 1,000,000,
the improvement comprising employing at least 4.3% of said mixture in the composition and employing in said mixture the tetrasodium pyrophosphate and tetrapotassium pyrophosphate in a respective ratio of 2.7:4.3 to 1:6 and sufficient tetrapotassium pyrophosphate to inhibit the occurrence of solid gritty particles of tetrasodium pyrophosphate in the composition.

3. In an oral composition containing an orally acceptable aqueous vehicle and, in approximate weight amounts and proportions,
   A. a mixture of tetrasodium pyrophosphate and tetrapotassium pyrophosphate;
   B. an amount of a fluoride ion source sufficient to supply 25 ppm to 5,000 ppm of fluoride ions; and
   C. about 0.05 to about 3% of a synthetic anionic polymeric polycarboxylate having a molecular weight of about 1,000 to about 1,000,000,
the improvement comprising employing 4.3% to 7% of said mixture in the composition and employing the tetrasodium pyrophosphate and tetrapotassium pyrophosphate in a respective ratio ranging from 2.7:4.3 to 1:6.

4. In an oral composition containing an orally acceptable aqueous vehicle and, in approximate weight amounts and proportions;
   A. 0–90% of a dentally acceptable polishing agent,
   B. amount of fluoride ion source sufficient to supply 223 ppm to 9,050 ppm of fluoride ions;
   C. an amount of at least one pyrophosphate source sufficient to provide at least 2.3% of pyrophosphate ion; and
   D. about 0.05 to about 3% of a synthetic anionic polymeric polycarboxylate having a molecular weight of about 1,000 to about 1,000,000.
wherein the pH of said composition is about 4.5 to about 10, the improvement comprising employing in said composition sodium ions and potassium ions in a respective ratio of 0.1:1 to 1.04:1.

5. The composition of claim 4 containing sodium ions and potassium ions in a respective ratio of 0.37:1 to 1.04:1.

6. The composition of any of claims 1 to 5 further containing up to 0.4% dialkali metal pyrophosphate.

7. The composition of any of claims 1 to 5 further containing up to 1% dialkali metal pyrophosphate.

8. The composition of any of claims 1 to 5 further containing an orally acceptable silica abrasive.

9. The composition of any of claims 1 to 5 in which the fluoride ion source comprises sodium fluoride.

10. The composition of any of claims 1 to 5 comprising a synthetic anionic polymeric polycarboxylate having a molecular weight of about 30,000 to about 500,000.

11. The composition of any of claims 1 to 5 wherein said polymeric polycarboxylate comprises a carboxyvinyl polymer.

12. The composition of any of claims 1 to 5 wherein said polymeric polycarboxylate comprises a copolymer of maleic anhydride or acid with another polymerizable ethylenically unsaturated monomer.

13. The composition of claim 12 wherein said monomer is methyl vinyl ether.

14. The composition of claim 13 wherein said copolymer has a molecular weight of about 70,000.

15. A method of inhibiting dental calculus comprising applying to dental surfaces an effective inhibiting amount of a composition as defined in claim 14.

16. A method of inhibiting dental calculus comprising applying to dental surfaces an effective inhibiting amount of a composition as defined in any of claims 1 to 5.

17. The composition of any of claims 1 to 5 in which said polycarboxylate is an ammonium or alkali metal salt.

18. The composition of claim 14 in which said copolymer is in the form of an ammonium or alkali metal salt.

19. A method of inhibiting dental calculus comprising applying to dental surfaces an effective inhibiting amount of a composition as defined in claim 18.

20. A method of inhibiting dental calculus comprising applying to dental surfaces an effective inhibiting amount of a composition as defined in claim 17.

* * * * *